United States Patent
van Doormalen

(10) Patent No.: US 10,219,465 B2
(45) Date of Patent: Mar. 5, 2019

(54) LEEK VARIETY NUN 10401 LEL

(71) Applicant: Nunhems B.V., AB Nunhem (NL)

(72) Inventor: Antonius Joseph Gerardus van Doormalen, EG Meijel (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/610,728

(22) Filed: Jun. 1, 2017

(65) Prior Publication Data

US 2017/0332596 A1 Nov. 23, 2017

(51) Int. Cl.
*A01H 5/10* (2018.01)
*A01H 6/04* (2018.01)

(52) U.S. Cl.
CPC .............. *A01H 5/10* (2013.01); *A01H 6/045* (2018.05)

(58) Field of Classification Search
None
See application file for complete search history.

(56) References Cited

U.S. PATENT DOCUMENTS

2013/0202775 A1\* 8/2013 van Doormalen ....... A01H 5/12
426/635

FOREIGN PATENT DOCUMENTS

| WO | 2013182646 A1 | 12/2013 |
| WO | 2014076249 A1 | 5/2014 |

OTHER PUBLICATIONS

"Guidelines for the conduct of tests for distinctness, uniformity and stability", UPOV (International Union for the Protection of New Varieties and Plants), TG/85/7; Apr. 9, 2008; http://www.upov.int/edocs/tgdocs/en/tg085.pdf.
Ren et al., "Shoot regeneration and ploidy variation in tissue culture of honeydew melon (*Cucmis melo* L. *inodorus*)", In Vitro Cell.Dev. Biol., 2013, vol. 49, pp. 223-229.
Colijn-Hooymans et al., "Competence for regeneration of cucumber cotyledons is restricted to specific developmental stages", Plant Cell, Tissue and Organ Culture, 1994, vol. 39, pp. 211-217.
Vos et al., "AFLP: a new technique for DNA fingerprinting", Nucleic Acid Research, 1995, vol. 23, No. 21 pp. 4407-4414.
Parvathaneni et al., "Fingerprinting in Cucumber and Melon (*Cucumis* spp.) Genotypes Using Morphological and ISSR Markers", J. Crop Sci. Biotech., 2011, vol. 14, No. 1, pp. 39-43.
Brotman et al., "Resistance gene homologues in melon are linked to genetic loci conferring disease and pest resistance", Theor Appl Genet, 2002, vol. 104, pp. 1055-1063.
Wijnker et al., "Hybrid recreation by reverse breeding in *Arabidopsis thahana*", Nature Protocols, 2014, vol. 9, pp. 761-772 DOI: doi:10.1038/nprot.2014.049.

\* cited by examiner

*Primary Examiner* — Vinod Kumar
(74) *Attorney, Agent, or Firm* — Arent Fox LLP

(57) ABSTRACT

The invention provides a new and distinct hybrid variety of leek, NUN 10401 LEL.

17 Claims, No Drawings

LEEK VARIETY NUN 10401 LEL

FIELD OF THE INVENTION

The present invention relates to the field of plant breeding and, more specifically, to the development of leek variety NUN 10401 LEL, also referred to as "NUN 10401", "NUN 10401 F1", "NUN 10401 hybrid", or "10401 LEL" or Chiefton and parts thereof and seeds from which the variety can be grown. The invention further relates to vegetative reproductions of NUN 10401 LEL, methods for in vitro tissue culture of NUN 10401 LEL explants and also to phenotypic variants of NUN 10401 LEL. The invention further relates to methods of producing a leaf of NUN 10401 LEL or of phenotypic variants of NUN 10401 LEL.

The goal of vegetable breeding is to combine various desirable traits in a single variety/hybrid. Such desirable traits may include greater yield, resistance to insects or pests, tolerance to heat and drought, better agronomic quality, higher nutritional value, growth rate and leaf properties.

Breeding techniques take advantage of a plant's method of pollination. There are two general methods of pollination: self-pollination and cross-pollination.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

Leek (*Allium ampeloprasum* var. *porrum* (L.) or *Allium porrum*) belongs to the Alliceae family and is used as a crop in diverse countries. Most of the commercially available leek varieties are leek hybrid plants. These leek hybrid plants are plants produced by crossing a selected leek population with another selected leek population. The leek hybrid plants provide advantages over open pollinated crossbreds, such as uniformity, vitality and disease tolerance, resulting in an increased use of leek hybrids in commercial leek productions. Leek hybrid plants are generally produced by a technique designated in the art as "nuclear male sterility". Nuclear male sterility is a form of male sterility wherein the genetic factor responsible for the observed sterility is encoded by the nuclear genome. The term "Male sterility" indicates that a plant has no fertile pollen and, because of this, the male sterile plant is incapable of self-pollination.

Rather than forming a tight bulb like the onion, the leek produces a long cylinder of bundled leaf sheaths which are generally blanched by pushing soil around them (trenching). They are often sold as small seedlings in flats which are started off early in greenhouses, to be planted out as weather permits. Once established in the field or garden, leeks are hardy; many varieties can be left in the ground during the winter to be harvested as needed.

Leek cultivars can mainly be divided in three types: Summer leek, Autumn leek and Winter leek. Summer leek is fast growing leek, leaf color is green. Harvest period is early summer to late summer/beginning of autumn. Autumn leek is medium fast to medium slow growing leek. Leaf color is dark green to blue-green. Varieties are more tolerant to low temperatures. Most genotypes in this type have a shorter shaft compared to the summer leek. Harvest period is early autumn, autumn, beginning of winter. Winter leek is slow growing leek. Foliage color is dark green mostly blue-green; varieties are tolerant to cold and to frost to some extent. Winter hardiness is good. Shafts are rather short. Harvest period is end of autumn, winter until early spring (just before bolting starts). The edible portions of the leek are the white base of the leaves (above the roots and stem base), the light green parts, and to a lesser extent the dark green parts of the leaves. One of the most popular uses is for adding flavor to stock. The use of a type of leek depends on the growth habit of said leek and a customer's preference for shape of leaves/the plant, and color.

While breeding efforts to date have provided a number of useful leek lines with beneficial traits, there remains a great need in the art for new varieties with further improved traits. Such plants would benefit farmers and consumers alike by improving crop yields and/or quality.

SUMMARY OF THE INVENTION

In one aspect of the invention, a seed of leek variety NUN 10401 LEL is provided, wherein a representative sample of said seed has been deposited under Accession Number NCIMB 43269. The leek seed of the invention may be provided as an essentially homogeneous population of leek seed. Therefore, seed of the invention may be defined as forming at least about 97% of the total seed, including at least about 98%, 99% or more of the seed. The population of leek seed may be particularly defined as being essentially free from other seed. The seed population may be separately grown to provide an essentially homogeneous population of leek plants according to the invention. Also encompassed are a plant grown from a seed of leek variety NUN 10401 LEL and a plant part thereof.

In another aspect the invention provides for a hybrid variety of *Allium ampeloprasum* called NUN 10401 LEL. The invention also provides for a seed or a plurality of seeds of the new variety, a plant produced from growing the seed of the new variety NUN 10401 LEL, and a progeny of any of these. Especially, a progeny retaining all or all but one, two or three of the "distinguishing characteristics" or all or all but one, two or three of the "morphological and physiological characteristics" or essentially all physiological and morphological characteristics of NUN 10401 LEL referred to herein, are encompassed herein as well as methods for producing these.

In one aspect, such progeny have all the physiological and morphological characteristics of leek variety NUN 10401 LEL when grown under the same environmental conditions. In another aspect such progeny have all or all but one, two or three the physiological and morphological characteristics as listed in Table 1 as leek variety NUN 10401 LEL when measured under the same environmental conditions (i.e. evaluated at significance levels of 1%, 5% or 10% significance, which can also be expressed as a p value).

In another aspect a plant of the invention or said progeny plants has/have 3, 4, 5, 6, 7, 8, or more or all of the distinguishing characteristics: 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color, in addition to 3, 4, 5, 6, 7, 8, or more, or all of the other (average) characteristics as listed in Table 1. NUN 10401 LEL is a long shafted leek.

Further, a leek leaf produced on a plant grown from these seeds is provided.

In yet another embodiment of the invention, a plant having one, two or three physiological and/or morphological characteristics which are different from those of NUN 10401 LEL and which otherwise has all the physiological and morphological characteristics of NUN 10401 LEL as listed in Table 1, wherein a representative sample of seed of variety NUN 10401 LEL has been deposited under Accession Number NCIMB 43269, is provided.

Further, a vegetatively propagated plant of variety NUN 10401 LEL, or a part thereof, is provided having all or all but one, two or three of the morphological and physiological characteristics of NUN 10401 LEL when grown under the same environmental conditions.

Also a plant part derived from variety NUN 10401 LEL is provided, wherein said plant part is selected from the group consisting of: a leaf, a part of a leaf, a harvested leaf, a fruit, a harvested fruit, a part of a fruit, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on NUN 10401 LEL, hypocotyl, cotyledon, a scion, a stock, a rootstock, a pistil, an anther, and a flower or a part thereof. Leaves are particularly important plant parts. In yet another aspect, a seed of NUN 10401 LEL is provided. In still another aspect, a seed growing or grown on a plant of NUN 10401 LEL are provided.

DEFINITIONS

"Leek" refers herein to plants of the species *Allium ampeloprasum*, and leaves thereof. The most commonly eaten part of a leek is the leaf "Cultivated leek" refers to plants of *Allium ampeloprasum* L, i.e. varieties, breeding lines or cultivars of the species *Allium ampeloprasum* L, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

The terms "leek plant designated NUN 10401 LEL", "NUN 10401", "10401 LEL" or "variety designated 10401 LEL" are used interchangeably herein and refer to a leek plant of variety NUN 10401 LEL, representative seed of which having been deposited under Accession Number NCIMB 43269.

A "seed of NUN 10401 LEL" refers to an F1 hybrid seed represented by the deposit with Accession Number NCIMB 43269. It contains an embryo of NUN 10401 LEL, or a "F1 hybrid embryo". When said seed is planted, it grows into a plant of NUN 10401 LEL.

A "seed grown on NUN 10401 LEL" refers to a seed grown on a mature plant of NUN 10401 LEL or inside a fruit of NUN 10401 LEL. The "seed grown on NUN 10401 LEL" contains tissues and DNA of the maternal parent, NUN 10401 LEL. The "seed grown on NUN 10401 LEL" contains an F2 embryo. When said seed is planted, it grows into a first generation progeny plant of NUN 10401 LEL.

"Tissue culture" refers to a composition comprising isolated cells of the same or a different type or a collection of such cells organized into parts of a plant. Tissue culture of various tissues of leek and regeneration of plants therefrom is well known and widely published (see, e.g., see, e.g., Ren et al., In Vitro Cell.Dev.Biol.—Plant (2013) 49:223-229; Colijn-Hooymans (1994), Plant Cell, Tissue and Organ Culture 39: 211-217). Similarly, the skilled person is well-aware how to prepare a "cell culture".

"UPOV descriptors" are the plant variety descriptors described for leek in the "Guidelines for the Conduct of Tests for Distinctness, Uniformity and Stability, TG/85/7 (Geneva 2008), as published by UPOV (International Union for the Protection of New Varieties and Plants, available on the world wide web at upov.int) and which can be downloaded from the world wide web at upov.int/edocs/tgdocs/en/tg085.pdf and is herein incorporated by reference in its entirety.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested leaves), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a harvested leaf, a part of a leaf, pollen, an ovule, an embryo, a petiole, a shoot or a part thereof, a stem or a part thereof, a root or a part thereof, a root tip, a cutting, a seed, a part of a seed, seedcoat or another maternal tissue which is part of a seed grown on NUN 10401 LEL, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant.

"Harvested plant material" refers herein to plant parts (e.g. a leaf detached from the whole plant) which have been collected for further storage and/or further use.

"Harvested seeds" refers to seeds harvested from a line or variety, e.g. produced after self-fertilization or cross-fertilization and collected.

"REFERENCE VARIETY" refers herein to variety Belton, a commercial variety from Nunhems B.V., which has been planted together with NUN 10401 LEL. Descriptors/characteristics of NUN 10401 LEL were compared to the descriptors of Belton.

A plant having "all the physiological and morphological characteristics" of a referred-to-plant means a plant having the physiological and morphological characteristics of the referred-to-plant when grown under the same environmental conditions, preferably in the same experiment; the referred-to-plant can be a plant from which it was obtained, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 or "all or all but one, two or three of the physiological and morphological characteristics" of Table 1.

For NUN 10401 LEL the distinguishing characteristics are 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color.

In certain embodiments the plant of the invention has all the physiological and morphological characteristics, except for certain characteristics mentioned, e.g. the characteristic(s) derived from a converted or introduced gene or trait and/or except for the characteristics which differ, for example a Single Locus Conversion or mutation.

In one embodiment, the invention relates to a Single Locus Converted plant of NUN 10401 LEL.

Similarity between different plants is defined as the number of morphological and/or physiological characteristics (or the characteristics as listed in Table 1 that are the same between the two plants that are compared when grown under the same environmental conditions. Numerical characteristics are considered "the same" when the value for a numeric characteristic is evaluated at significance levels of 1%, 5% or 10% significance level, or at p≤0.05 using one way Analysis of variance (ANOVA), a standard methods known to the skilled person. Non-numerical or "type" characteristic are considered "the same" if identical or having the same value when scored for characteristics comprising a.o. UPOV descriptors, if the plants are grown under the same conditions. It is understood that "significant" differences refer to statistically significant differences, when comparing the characteristic between two plant lines or varieties when grown under the same conditions. Preferably at least about 10, 15, 20, 50 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10% or evaluated at p≤0.05 using ANOVA, when measured in plants grown under the same environmental conditions.

"Distinguishing characteristics" or "distinguishing morphological and/or physiological characteristics" refers herein the characteristics which are distinguishing between NUN 10401 LEL and other leek varieties, such as REFERENCE VARIETY, when grown under the same environmental conditions, especially the following characteristics: 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color. In one aspect, the distinguishing characteristics further include at least one, two, three or more (or all) of the characteristics listed in Table 1. All numerical distinguishing characteristics are statistically significantly different at p≤0.05.

Thus, a leek plant "comprising the distinguishing characteristics of "NUN 10401 LEL" refers herein to a leek plant which does not differ significantly from NUN 10401 LEL in characteristics 1) to 10) above. In yet a further aspect the leek plant further does not differ in all or all but one, two, three, four, five or six characteristics listed in Table 1.

The physiological and/or morphological characteristics mentioned above are commonly evaluated at significance levels of 1%, 5% or 10% or evaluated at p≤0.05 using ANOVA, when measured under the same environmental conditions. For example, a progeny plant of NUN 10401 LEL may have one or more (or all) of the essential physiological and/or morphological characteristics of NUN 10401 LEL listed in Table 1, as determined at the 5% significance level when grown under the same environmental conditions.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or obtained from (e.g. by cutting of) a fruit, a harvested fruit, a part of a fruit, a leaf, a harvested leaf, a part of a leaf, pollen, an ovule, a cell, a petiole, a shoot or a part thereof, a stem or a part thereof, a root or a part thereof, a root tip, a cutting, a seed, hypocotyl, cotyledon, a scion, a stock, a rootstock, a pistil, an anther, and a flower or a part thereof, etc. When a whole plant is regenerated by vegetative propagation, it is also referred to as a vegetative propagation.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition. These terms are also used to describe plants showing some symptoms but that are still able to produce marketable product with an acceptable yield.

"Locus" (plural loci) refers to the specific location, place or site of a DNA sequence on a chromosome, where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristics of a plant, cell or organism, which characteristics are the manifestation of gene expression.

Haploid" refers to a cell or organism having one set of the two sets of chromosomes in a diploid.

"Diploid" refers to a cell or organism having two sets of chromosomes.

"Planting" or "planted" refers to seeding (direct sowing) or transplanting seedlings (plantlets) into a field by machine or hand.

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one leek line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". Backcrossing can also be applied to a parental line.

"Progeny" as used herein refers to a plant derived from a plant designated NUN 10401 LEL. A progeny may be obtained by regeneration of cell culture or tissue culture or parts of a plant designated NUN 10401 LEL or selfing of a plant designated NUN 10401 LEL or by producing seeds of a plant designated NUN 10401 LEL (such a progeny is not genetically identical to the parent, unless both parents are of the same highly homozygous line). In further embodiments, progeny may also encompass plants obtained from crossing of at least one plant designated NUN 10401 LEL with another leek plant of the same or another variety or (breeding) line, or wild leek plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to leek plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a leek variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a leek plant by transformation. A plant comprising a transgene stably integrated into its genome is referred to as "transgenic plant".

"Linkage" refers to a phenomenon wherein alleles on the same chromosome tend to segregate together more often than expected by chance if their transmission was independent.

"Haploid" refers to a cell or organism having one set of the two sets of chromosomes in a diploid. "Diploid" refers to a cell or organism having two sets of chromosomes. "Polyploid" refers to a cell or organism having three or more complete sets of chromosomes. "Triploid" refers to a cell or organism having three sets of chromosomes. "Tetraploid" refers to a cell or organism having four sets of chromosomes.

"Marker" refers to a readily detectable phenotype, preferably inherited in codominant fashion (both alleles at a locus in a diploid heterozygote are readily detectable), with no environmental variance component, i.e., a heritability of 1.

"Yield" means the total weight of all leek leaves harvested per hectare of a particular line or variety. It is understood that "yield" expressed as weight of all leek leaves harvested per hectare can be obtained by multiplying the number of plants per hectare times the "yield per plant".

"Marketable yield" means the total weight of all marketable leek leaves, especially leaves that is not damaged or diseased, harvested per hectare of a particular line or variety.

"Substantially equivalent" refers to a characteristic that, when compared, does not show a statistically significant difference (e.g., p=0.05) from the mean.

The term "mean" refers to the arithmetic mean of several measurements. The skilled person understands that the appearance of a plant depends to some extent on the growing conditions of said plant. Thus, the skilled person will know typical growing conditions for leek described herein. The mean, if not indicated otherwise within this application, refers to the arithmetic mean of measurements on at least 10 different, randomly selected plants of a variety or line.

DETAILED DESCRIPTION

The present invention relates to a *Allium ampeloprasum* variety, referred to as NUN 10401 LEL, which—when compared to REFERENCE VARIETY Belton—has a higher/ 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color. Also encompassed by the present invention are progeny plants having all but 1, 2, or 3 of the morphological and/ physiological characteristics of NUN 10401 LEL and methods of producing plants in accordance with the present invention.

A leek plant of NUN 10401 LEL differs from the most similar comparison variety REFERENCE VARIETY in one or more characteristics (referred herein to as "distinguishing characteristics" or "distinguishing morphological and/or physiological characteristics" (or essential physiological and/or morphological characteristics) selected from: 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color.

NUN 10401 LEL may further exhibit at least one further trait selected from the group consisting of a) stiffer leaf type than Belton, b) waxier leaf type than Belton.

Thus, in one aspect, the invention provides a seed of the leek variety designated NUN 10401 LEL wherein a representative sample of seeds of said variety was deposited under the Budapest Treaty, with Accession number NCIMB 43269.

In another aspect, the invention provides for a leek plant of variety NUN 10401 LEL, a representative sample of seed from said variety has been deposited under the Budapest Treaty, with Accession number NCIMB 43269. In other aspects, the invention provides for a leaf of leek variety NUN 10401 LEL, or a plant part, such as pollen, flowers, shoots or cuttings of variety NUN 10401 LEL or parts thereof.

A seed of NUN 10401 LEL is obtainable by crossing the male parent of NUN 10401 LEL with the female parent of NUN 10401 LEL and harvesting the seeds produced on the female parent. The resultant NUN 10401 LEL seeds can be grown to produce NUN 10401 LEL plants. In one embodiment a seed or a plurality of seeds of NUN 10401 LEL are packaged into containers of any size or type (e.g., bags, cartons, cans, etc.). The seed may be disinfected, primed and/or treated with various compounds, such as seed coatings or crop protection compounds.

Also provided is a plant of leek variety NUN 10401 LEL, or a leaf or other plant part thereof, produced from a seed, wherein a representative sample of said seeds has been deposited under the Budapest Treaty, with Accession Number NCIMB 43269. Also included is a cell culture or tissue culture produced from such a plant.

In one embodiment the invention provides a leek plant regenerated from the tissue or cell culture of NUN 10401 LEL, wherein the plant has all or all but one, two or three of of the physiological and morphological characteristics of NUN 10401 LEL as listed in Table 1 when determined at the 5% significance level or evaluated at $p \leq 0.05$ using ANOVA. It is understood that a tissue or cell culture of NUN 10401 LEL can be obtained from any plant part of said variety. In another embodiment, the invention provides a leek plant regenerated from the tissue or cell culture of NUN 10401 LEL, wherein the plant has all or all but one, two or three of the physiological and morphological characteristics of NUN 10401 LEL when determined at the 5% significance level or evaluated at $p \leq 0.05$ using ANOVA.

A plants of NUN 10401 LEL can be produced by seeding directly in the soil (e.g., field) or by germinating the seeds in controlled environment conditions (e.g., greenhouses) and then transplanting the seedlings into the field. For example, the seed can be sown into prepared seed beds where they will remain for the entire production of the crop. Leek can also be grown entirely in greenhouses.

In one embodiment any plant of the invention comprises at least 6, 7, 8, 9 or all of the following morphological and/or physiological characteristics (i.e. distinguishing characteristics (average values; measured at harvest or market maturity, preferably as indicated Table 1 (unless indicated otherwise), when grown under the same environmental conditions): 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color.

In still another aspect the invention provides a method of producing a leek plant, comprising crossing a plant of leek variety NUN 10401 LEL with a second leek plant one or more times, and selecting progeny from said crossing. In one embodiment of the invention, the first step in "crossing" comprises planting seeds of a first and a second parent leek plant, often in proximity so that pollination will occur for example, mediated by insect vectors. Alternatively, pollen can be transferred manually. Where the plant is self-pollinated, pollination may occur without the need for direct human intervention other than plant cultivation.

In yet another aspect the invention provides a method of producing a leek plant, comprising selfing a plant of leek variety NUN 10401 LEL one or more times, and selecting progeny from said selfing.

In other aspects, the invention provides for a progeny of variety NUN 10401 LEL such as progeny obtained by further breeding NUN 10401 LEL. Further breeding NUN 10401 LEL includes selfing NUN 10401 LEL one or more times and/or cross-pollinating NUN 10401 LEL with another leek plant or variety one or more times. In particular, the invention provides for progeny that retain all the essential morphological and physiological characteristics of NUN 10401 LEL or that retain one or more of the distinguishing characteristics of the leek type described further above and when grown under the same environmental conditions. In another aspect, the invention provides for a vegetative reproduction of the variety and a plant having all but 1, 2, or 3 of the physiological and morphological characteristics of NUN 10401 LEL (e.g. as listed in Table 1).

The morphological and/or physiological differences between a plant according to the invention, i.e. NUN 10401 LEL or progeny thereof, or a plant having all but 1, 2, or 3 of the physiological and morphological characteristics of NUN 10401 LEL (as listed in Table 1); and another known variety can easily be established by growing NUN 10401 LEL next to the other variety (in the same field, under the same environmental conditions), preferably in several locations which are suitable for said leek cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18'807", USA, whereby various characteristics, for example maturity, days from seeding to harvest, plant habit, plant attitude, leaf shape, leaf color, disease resistance, insect resistance, can be measured and directly compared for species of *Allium*.

The morphological and physiological characteristics (and the distinguishing characteristics) of NUN 10401 LEL are provided in the Examples, in Table 1. Encompassed herein is also a plant derivable from NUN 10401 LEL (e.g. by selfings and/or crossing and/or backcrossing with NUN 10401 LEL and/or progeny thereof) comprising all or all but one, two or three of the physiological and morphological characteristics of NUN 10401 LEL listed in Table 1 as determined at the 5% significance level or evaluated at $p \leq 0.05$ using ANOVA when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of leaves can be compared, such as cold storage holding quality, disease resistance and color.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In a preferred embodiment, the invention provides for a leek leaf of variety NUN 10401 LEL, or a part of said leaf. In another embodiment, the invention provides for a container comprising or consisting of a plurality of harvested leek leaves or parts of leaves of NUN 10401 LEL, or leaves of progeny thereof, or leaves of a variety having all but 1, 2, or 3 of the morphological and physiological characteristics of NUN 10401 LEL.

In yet a further embodiment, the invention provides for a method of producing a new leek plant. The method comprises crossing a plant of the invention NUN 10401 LEL, or a plant comprising all but 1, 2, or 3 of the morphological and physiological characteristics of NUN 10401 LEL (as listed in Table 1), or a progeny plant thereof, either as male or as female parent, with a second leek plant (or a wild relative of leek) one or more times, and/or selfing a leek plant according to the invention i.e. NUN 10401 LEL, or a progeny plant thereof, one or more times, and selecting progeny from said crossing and/or selfing. The second leek plant may for example be a line or variety of the species *Allium ampeloprasum*, or other *Allium* species or even other Alliceae species.

Progeny are either the generation (seeds) produced from the first cross of the hybrid with another plant (F2) or selfing of the hybrid (S1), or any further generation produced by crossing and/or selfing (F2, F3, etc.) and/or backcrossing (BC1, BC2, etc.) one or more selected plants of the F2 and/or S1 and/or BC1 generation (or plants of any further generation, e.g. the F3) with another leek plant (and/or with a wild relative of leek). Progeny can also refer to a vegetative propagation or a regenerated plant of the invention Progeny may have all the physiological and morphological characteristics of leek variety NUN 10401 LEL when grown under the same environmental conditions and/or progeny may have (be selected for having) one or more of the distinguishing characteristics of leek of the invention. Using common breeding methods such as backcrossing or recurrent selection, one or more specific characteristics may be introduced into NUN 10401 LEL, to provide or a plant comprising all but 1, 2, or 3 or more of the morphological and physiological characteristics of NUN 10401 LEL (as listed in Table 1).

The invention provides for methods of producing plants which retain all the morphological and physiological characteristics of NUN 10401 LEL. The invention provides also for methods of producing a plant comprising all but 1, 2, or 3 or more of the morphological and physiological characteristics of NUN 10401 LEL (e.g. as listed in Table 1), but which are still genetically closely related to NUN 10401 LEL. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 10401 LEL if its DNA fingerprint is at least 80%, 90%, 95% or 98% identical to the fingerprint of NUN 10401 LEL. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1) : 39~43). The invention also provides a plant and a variety obtained by these methods. Plants may be produced by crossing and/or selfing, or alternatively, a plant may simply be identified and selected amongst NUN 10401 LEL plants, or progeny thereof, e.g. by identifying a variant within NUN 10401 LEL or progeny thereof (e.g. produced by selfing) which variant differs from NUN 10401 LEL in one, two or three of the morphological and/or physiological characteristics (e.g. in one, two or three distinguishing characteristics), e.g. those listed in Table 1 or others. In one embodiment the invention provides a leek plant having a Jaccard's Similarity index with NUN 10401 LEL of at least 0.8, e.g. at least 0.85, 0.9, 0.95, 0.98 or even at least 0.99.

The present invention also provides a leek seed and a plant produced by a process that comprises crossing a first parent leek plant with a second parent leek plant, wherein at least one of the first or second parent leek plants is a hybrid plant provided herein, such as from variety NUN 10401 LEL. In another embodiment of the invention, leek seed and plants produced by the process are second filial generation (F2) leek seed and plants produced by crossing a plant in accordance with the invention with another, distinct plant. The present invention further contemplates plant parts of such an F2 leek plant, and methods of use thereof. Therefore, certain exemplary embodiments of the invention provide an F2 leek plant and seed thereof.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of NUN 10401 LEL (i.e. is progeny of NUN 10401 LEL), because the seed coat is genetically identical to NUN 10401 LEL. In one embodiment, the present invention relates to a seed coat comprising maternal tissue of NUN 10401 LEL. In another embodiment the invention relates to a leek seed comprising a seed coat that comprises maternal tissue from NUN 10401 LEL.

By crossing and/or selfing also (one or more) single traits may be introduced into the variety of the invention i.e. NUN 10401 LEL (e.g., using backcrossing breeding schemes), while retaining the remaining morphological and physiological characteristics of NUN 10401 LEL and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 10401 LEL by breeding with NUN 10401 LEL.

Alternatively, a single trait converted plant or single locus converted plant may be produced by the following steps
  a. obtaining a cell or tissue culture of cells of NUN 10401 LEL;

b. genetically transforming or mutating said cells;
c. growing the cells into a plant; and
d. optionally selecting a plant that contains the desired single locus conversion The skilled person is familiar with various techniques for genetically transforming a single locus in a plant cell, or mutating said cells.

Any trait can be introduced by the method. In a preferred embodiment, pest or disease resistance genes may be introduced into a plant according to the invention, i.e. NUN 10401 LEL, progeny thereof or into a plant comprising all but 1, 2, or 3 or more of the morphological and physiological characteristics of NUN 10401 LEL (e.g. as listed in Table 1). Resistance to one or more of the following diseases or pests is preferably introduced into plants of the invention: Aphid resistance, Pickle Worm, Darkling Ground Beetle, Banded Cucumber Beetle, Mite, Western Spotted Cucumber Beetle, Leek Leafhopper, Leek Worm, Western Striped Cucumber Beetle or Leek Leafminer, *Thrips tabaci*, Leek moth and Onion fly. Other resistance genes, against pathogenic viruses, fungi, bacteria, nematodes, insects or other pests may also be introduced.

Thus, invention also provides a method for developing a leek plant in a leek breeding program, using a leek plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 10401 LEL or progeny thereof, or a plant comprising all but 1, 2, or 3 or more of the morphological and physiological characteristics of NUN 10401 LEL (e.g. as listed in Table 1), with a different leek plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Brotman et al., Theor Appl Genet (2002) 104:1055-1063). For breeding methods in general see Principles of Plant Genetics and Breeding, 2007, George Acquaah, Blackwell Publishing, ISBN-13: 978-1-4051-3646-4.

The invention also provides a leek plant comprising at least a first set of the chromosomes of leek variety NUN 10401 LEL, a sample of seed of said variety having been deposited under Accession Number NCIMB 43269; optionally further comprising a single locus conversion, wherein said plant has essentially all of the morphological and physiological characteristics of the plant comprising at least a first set of the chromosomes of leek NUN 10401 LEL. In another embodiment, this single locus conversion confers a trait selected from the group consisting of male sterility, herbicide tolerance, insect resistance, pest resistance, disease resistance, environmental stress tolerance, leek rust resistance modified carbohydrate metabolism and modified protein metabolism.

In one embodiment, NUN 10401 LEL may also be mutated (by e.g. irradiation, chemical mutagenesis, heat treatment, etc.) and mutated seeds or plants or cells may be selected in order to change one or more characteristics of NUN 10401 LEL. Methods such as TILLING may be applied to leek populations in order to identify mutants. Similarly, NUN 10401 LEL may be transformed and regenerated, whereby one or more chimeric genes are introduced into the variety or into a plant comprising all but 1, 2, 3, or more of the morphological and physiological characteristics (e.g. as listed in Table 1). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 10401 LEL, or progeny thereof, by transforming NUN 10401 LEL or progeny thereof with a transgene that confers the desired trait, wherein the transformed plant retains all the phenotypic and/or morphological and/or physiological characteristics of NUN 10401 LEL or the progeny thereof and contains the desired trait.

The invention also provides a plant or a cell of a leek plant a desired trait produced by mutating a leek plant of variety NUN 10401 LEL or a cell thereof and selecting a plant the desired trait, wherein the mutated plant retains all or all but one, two or three of the phenotypic and morphological characteristics of variety NUN 10401 LEL, optionally as described in Table 1, and contains the desired trait and wherein a representative sample of seed of variety NUN 10401 LEL has been deposited under Accession Number NCIMB 43269.

In a further embodiment, the desired trait is selected from the group consisting of yield, storage properties, color, flavor, male sterility, herbicide tolerance, insect resistance, pest resistance, disease resistance, environmental stress tolerance, leek rust resistance, modified carbohydrate metabolism, modified protein metabolism and ripening.

The invention also provides a plant having one, two or three physiological and/or morphological characteristics which are different from those of NUN 10401 LEL and which otherwise has all the physiological and morphological characteristics of NUN 10401 LEL, wherein a representative sample of seed of variety NUN 10401 LEL has been deposited under Accession Number NCIMB 43269. In particular variants which differ from NUN 10401 LEL in none, one, two or three of the characteristics mentioned in Table 1 are encompassed.

In one aspect, the the plant having one, two or three physiological and/or morphological characteristics which are different from those of NUN 10401 LEL and which otherwise has all the physiological and morphological characteristics of NUN 10401 LEL differs from NUN 10401 LEL in one, two or three of the distinguishing morphological and/or physiological characteristics selected from 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color.

In another embodiment the plant having one, two or three physiological and/or morphological characteristics which are different from those of NUN 10401 LEL and which otherwise has all the physiological and morphological characteristics of NUN 10401 LEL may differ from NUN 10401 LEL in one, two or three morphological or physiological characteristic other than the "distinguishing morphological and/or physiological characteristics" (or essential physiological and/or morphological characteristics) of NUN 10401 LEL selected from: 1) average Plant height; 2) average Plant length; 3) average Shaft length; 4) average Shaft diameter; 5) average Leaf blade length; 6) average Leaf blade width; 7) average Leaf angle; 8) typical habit; 9) average Shaft ratio; and 10) typical leaf color.

Leeks according to the invention, such as the variety NUN 10401 LEL, or its progeny, or a plant having all physiological and/or morphological characteristics but one, two or three which are different from those of NUN 10401 LEL, can also be reproduced using vegetative reproduction methods. Therefore, the invention provides for a method of producing plants, or a part thereof, of variety NUN 10401 LEL, comprising vegetative propagation of variety NUN 10401 LEL. Vegetative propagation comprises regenerating a whole plant from a plant part of variety NUN 10401 LEL (or from its progeny or from or a plant having all physiological and/or morphological characteristics of NUN 10401 LEL but one, two or three, which are different), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 10401 LEL (or from its progeny or from or a plant having all but one, two or three physiological and/or morphological characteristics of NUN 10401 LEL, or a part thereof, having one or more distinguishing characteristics and/or all the morphological and physiological characteristics of NUN 10401 LEL), when grown under the same environmental conditions.

A part of NUN 10401 LEL (or of its progeny or of a plant having all physiological and/or morphological characteristics but one, two or three which are different from those of NUN 10401 LEL) encompasses any cells, tissues, organs obtainable from the seedlings or plants, such as but not limited to: a leek leaf or a part thereof, a cutting, hypocotyl, cotyledon, seedcoat, pollen and the like. Such parts can be stored and/or processed further. Encompassed are therefore also food or feed products comprising one or more of such parts, preferably wherein the plant part can be identified as a part of the plant of the invention. Preferably, the plant part is a leek leaf or part thereof and/or a plurality of leaves or frozen leaves or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, chopped, cooked, roasted, in a sauce, in a sandwich, pasted, puréed or concentrated, blanched and/or frozen, etc.

In one embodiment, the invention provides for extracts of a plant described herein and compositions comprising or consisting of such extracts. In a preferred embodiment, the extract consists of or comprises tissue of a plant described herein or is obtained from such tissue.

For example, containers such as cans, boxes, crates, bags, cartons, Modified Atmosphere Packagings, films (e.g. biodegradable films), etc. comprising a plant or a parts of a plant (fresh and/or processed) described herein or a seed of NUN 10401 LEL are also provided herein.

Marketable leek leaves are generally sorted by size and quality after harvest, optionally in batches.

In one aspect a haploid plant and/or a doubled haploid plant of NUN 10401 LEL, or a plant having all but one, two or three physiological and/or morphological characteristics of NUN 10401 LEL, or progeny of any of these, are encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or doubled haploid plants are obtained from NUN 10401 LEL that, when combined, make a set of parents of NUN 10401 LEL are encompassed herein.

Using methods known in the art like "reverse synthesis of breeding lines", it is possible to produce parental lines for a hybrid plant such as NUN 10401 LEL; where normally the hybrid is produced from the parental lines. Such methods are based on the segregation of individual alleles in the spores produced by a desired plant and/or in the progeny obtained from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi: 10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 10401 LEL) comprising the step of making doubled haploid cells from haploid cells from the plant of the invention (NUN 10401 LEL) or a seed of that plant; and optionally crossing these parental lines to produce and collect seeds. In another aspect, the invention relates to a combination of parental lines produced by this method. In still another aspect said combination of parental lines can be used to produce a seed or plant of NUN 10401 LEL when these parental lines are crossed. In still another aspect, the invention relates to a combination of parental lines from which a seed or plant having all physiological and/or of NUN 10401 LEL morphological characteristics but one, two or three which are different can be produced or in another aspect, wherein a seed or plant having the distinguishing characteristics 1)-10) of NUN 10401 LEL, as herein defined, can be produced when grown under the same environmental conditions. In still another aspect, the invention relates to a combination of parental lines from which a seed or plant having all the characteristics of NUN 10401 LEL as defined in Table 1 when grown under the same conditions can be produced.

In another alternative aspect, the invention provides a method of introducing a single locus conversion or single trait conversion or a desired trait into NUN 10401 LEL comprising:
  a. obtain a combination of a male and a female parental line of NUN 10401 LEL,
  b. introduce a single locus conversion in at least one of the parents of step a;
  c. crossing the converted parent with the other parent of step a to obtain seed of NUN 10401 LEL A combination of a male and a female parental line of NUN 10401 LEL can be generated by methods described herein, for example through reverse breeding;

Step b) of the above method—introduce a single locus conversion in at least one of the parents of step a—may be done through the following method:
  i. obtaining a cell or tissue culture of cells of the parental line of NUN 10401 LEL;
  ii. genetically transforming or mutating said cells;
  iii. growing the cells into a plant; and
  iv. optionally selecting plants that contain the single locus conversion, the single trait conversion or the desired trait.

The invention further relates to plants obtained by this method.

Step b) of the above method—introduce a single locus conversion in at least one of the parents of step a—may be done through the following method:
  i. crossing the parental line of NUN 10401 LEL with a second leek plant comprising the single locus conversion, the single trait conversion or the desired trait;
  ii. selecting first generation progeny plants of said crossing that contain the single locus conversion, the single trait conversion or the desired trait;
  iii. crossing said selected progeny plants of step ii with the parental line of step i, to produce a backcross progeny plant;
  iv. selecting backcross progeny plants comprising the single locus conversion, the single trait conversion or the desired trait and otherwise all or all but one, two or three of the morphological and physiological characteristics the parental line of step i to produce selected backcross progeny plants; and
  v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is pest resistance or disease resistance.

Any trait can be introduced. In one embodiment the trait is disease resistance and the resistance is conferred to Aphid resistance, Pickle Worm, Darkling Ground Beetle, Banded Cucumber Beetle, Mite, Western Spotted Cucumber Beetle, Leek Leafhopper, Leek Worm, Western Striped Cucumber Beetle or Leek Leafminer, *Thrips tabaci*, Leek moth and Onion fly.

Also provided are plant parts obtained from variety NUN 10401 LEL (or from its progeny or from a plant having all but one, two or three physiological and/or morphological characteristics which are different from those of NUN 10401 LEL, or from a vegetatively propagated plant of NUN 10401 LEL (or from its progeny or from a plant having all but one, two or three physiological and/or morphological characteristics which are different from those of NUN 10401 LEL), being selected from the group consisting of a fruit, a harvested fruit, a part of a fruit, a leaf, a harvested leaf, part of a leaf, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on NUN 10401 LEL, hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium All documents (e.g., patent publications) are herein incorporated by reference in their entirety. Cited references:
Ren et al., In Vitro Cell.Dev.Biol.—Plant (2013) 49:223-229
Colijn-Hooymans (1994), Plant Cell, Tissue and Organ Culture 39: 211-217
"UPOV descriptors" are the plant variety descriptors described for leek in the "Guidelines for the Conduct of Tests for Distinctness, Uniformity and Stability, TG/85/7 (Geneva 2008), as published by UPOV (International Union for the Protection of New Varieties and Plants, available on the world wide web at upov.int) and which can be downloaded from the world wide web at upov.int/edocs/tgdocs/en/tg085.pdf and is herein incorporated by reference in its entirety.
Vos et al. 1995, Nucleic Acid Research 23: 4407-4414
Parvathaneni et al., J. Crop Sci. Biotech. 2011 (March) 14 (1) : 39-43
Brotman et al., Theor Appl Genet (2002) 104:1055-1063
WO2014076249
WO2013182646
Nature Protocols Volume: 9, Pages: 761-772 (2014) DOI: doi:10.1038/nprot.2014.049

EXAMPLES

Development of NUN 10401 LEL

The hybrid NUN 10401 LEL was developed from a male and female proprietary inbred line of Nunhems. The female and male parents were crossed to produce hybrid (F1) seeds of NUN 10401 LEL The seeds of NUN 10401 LEL can be grown to produce hybrid plants and parts thereof (e.g. leek leaf). The hybrid NUN 10401 LEL can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 10401 LEL is uniform and stable.

Deposit Information

A total of 2500 seeds of the hybrid variety NUN 10401 LEL were deposited according to the Budapest Treaty by Nunhems B.V. on Nov. 13, 2018, at the NCIMB Ltd., Ferguson Building, Craibstone Estate, Bucksburn, Aberdeen AB21 9YA, United Kingdom (NCIMB). The deposit has been assigned NCIMB number 43269. A deposit of NUN 10401 LEL and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 10401 LEL is referred to as REFERENCE VARIETY, a variety from Nunhems B.V. with the commercial name Belton. In Table 1 and 2 a comparison between NUN 10401 LEL and REFERENCE VARIETY is shown based on a trial in the USA. Trial location: Acampo, Calif., USA; N38.192873 W121.232637. Transplanting date for NUN 10401 LEL: 17 Jun. 2016.

Two replications of 50 plants each, from which 15 plants or plant parts were randomly selected, were used to measure characteristics. In Table 1 the characteristics of NUN 10401 LEL (this application) and reference Belton (commercial variety) are listed.

In accordance with one aspect of the present invention, there is provided a plant having the physiological and morphological characteristics of leek variety NUN 10401 LEL as presented in Table 1, 2 and 3.

TABLE 1

| Descriptor | Application Variety NUN 10401 LEL | Reference Variety Belton |
|---|---|---|
| 1. Harvest time | | |
| Days from seeding to harvest | 165 | 165 |
| 2. Plant | | |
| Plant height in cm | 60.88 | 67.17 |
| Plant length in cm (at harvest) | 67.53 | 76.92 |
| Foliage attitude: 1 = erect (Reese); 2 = semi-erect (Linex); 3 = horizontal (De Carentan 2) | 1 | 1 |
| 3. Shaft (Column) | | |
| Shaft length (base of plant above roots to divergence of the 1ˢᵗ non-senescing leaf) in cm | 9.25 | 9.53 |
| Shaft diameter in mm | 26.5 | 24.14 |
| Shaft ratio length/diameter | 3.49 | 3.95 |
| Shaft bulb formation: 1 = absent or very weak; 2 = weak; 3 = medium; 4 = strong; 5 = very strong | 1 | 1 |
| 4. Leaf blade | | |
| Leaf blade bending: 1 = strong (Blauwgroene winter); 2 = medium (Flextan); 3 = weak (Bell) | 3 | 3 |
| Leaf blade length in cm | 44.95 | 54.29 |
| Leaf blade width in cm | 4.62 | 4.84 |
| Leaf angle (degrees from column) | 35.8 | 45.13 |
| Leaf blade color: 1 = yellow green (Jaune gros du Poitou); 2 = green (Premier); 3 = gray green (Zwitserse Reuzen); blue green (Blauwgroene Winter) | 3 (RHS Greyed green N189A) | 3 (RHS Green N137A) |
| Leaf blade color intensity: 1 = light; 2 = medium; 3 = dark | 3 | 2 |
| Leaf blade anthocyanin coloration: 1 = absent or very weak; 2 = weak; 3 = medium; 4 = strong; 5 = very strong | 1 | 1 |
| Leaf blade waxiness: 1 = absent or very weak (Kingston); 2 = weak (Carlton); 3 = medium (Linx); 4 = strong (Flextan); 5 = very strong | 3 to 4 | 3 |

Table 1 contains typical values. Values may vary due to environment. Other values that are substantially equivalent are also within the scope of the invention. N.A.=not applicable; n.r.=not recorded.

What is claimed is:

1. A plant, plant part or seed of leek variety NUN 10401 LEL, wherein a representative sample of said seed has been deposited under Accession Number NCIMB 43269.

2. The plant part of claim 1, wherein said plant part is a leaf, a pollen, an ovule, a fruit, a cutting, a flower or a cell.

3. A seed grown on the plant of claim 1.

4. A tissue or cell culture of regenerable cells of the plant of claim 1.

5. The tissue or cell culture according to claim 4, comprising cells or protoplasts from said plant part, wherein the plant part is a leaf, a part of a leaf, a fruit, a part of a fruit, a pollen, an ovule, a cell, a petiole, a shoot or a part thereof, a stem or a part thereof, a root or a part thereof, a root tip, a cutting, a hypocotyl, a cotyledon, a pistil, an anther, or a flower or a part thereof.

6. A leek plant regenerated from the tissue or cell culture of claim 4, wherein the regenerated plant has all of the physiological and morphological characteristics of the plant of leek variety NUN 10401 LEL, wherein a representative sample of seed of said variety has been deposited under Accession Number NCIMB 43269.

7. A method of producing the plant or a part thereof of claim 1, comprising vegetative propagation of said plant of leek variety NUN 10401 LEL.

8. The method of claim 7, wherein said vegetative propagation comprises regenerating a whole plant from a plant part of said leek variety NUN 10401 LEL.

9. The method of claim 7, wherein said part is a cutting, a cell culture or a tissue culture.

10. A vegetative propagated plant or a part thereof of claim 1, having all of the physiological and morphological characteristics of said leek variety NUN 10401 LEL when grown under the same environmental conditions.

11. A method of producing a leek plant, said method comprising crossing the plant of claim 1 with a second leek plant one or more times, and selecting progeny from said crossing.

12. A food or feed product comprising the plant part of claim 2.

13. A leek plant comprising at least a first set of the chromosomes of the plant of leek variety NUN 10401 LEL, wherein a representative sample of seed of said variety has been deposited under Accession Number NCIMB 43269, and wherein said leek plant comprising said first set of the chromosomes has all of the physiological and morphological characteristics of said leek variety NUN 10401 LEL.

14. A plant of leek variety NUN 10401 LEL, further comprising a single locus conversion, wherein a representative sample of seed of said leek variety NUN 10401 LEL has been deposited under Accession Number NCIMB 43269, and having all of the morphological and physiological characteristics of said leek variety NUN 10401 LEL when grown under the same environmental conditions.

15. A method of producing a leek plant having a desired trait, wherein the method comprises mutating a leek plant of variety NUN 010401 LEL and selecting a mutated leek plant with the desired trait, wherein the mutated leek plant retains all of the morphological and physiological characteristics of the leek variety NUN 10401 LEL and additionally contains the desired trait, and wherein a representative sample of seed of said leek variety NUN 10401 LEL has been deposited under Accession Number NCIMB 43269.

16. The method of claim 15, wherein the desired trait is selected from the group consisting of male sterility, herbicide tolerance, insect resistance, pest resistance, disease resistance, environmental stress tolerance, leek rust resistance, modified carbohydrate metabolism, modified protein metabolism and ripening.

17. The plant of leek variety NUN 10401 LEL of claim 14, wherein the single locus conversion confers a trait of male sterility, herbicide tolerance, insect resistance, pest resistance, disease resistance, environmental stress tolerance, modified carbohydrate metabolism or modified protein metabolism.

* * * * *